United States Patent [19]

Chand

[11] Patent Number: 4,948,496

[45] Date of Patent: Aug. 14, 1990

[54] GAS SENSOR

[75] Inventor: Ramesh Chand, Woodland Hills, Calif.

[73] Assignee: G C Industries, Chatsworth, Calif.

[21] Appl. No.: 351,282

[22] Filed: May 4, 1989

Related U.S. Application Data

[63] Continuation of Ser. No. 891,233, Jul. 29, 1986, abandoned.

[51] Int. Cl.$^5$ .............................................. G01N 27/31
[52] U.S. Cl. ..................................... 204/408; 204/415
[58] Field of Search ............... 204/408, 415, 1 P, 403; 128/635

[56] References Cited

U.S. PATENT DOCUMENTS

| | | | |
|---|---|---|---|
| 3,239,444 | 3/1966 | Heldenbrand | 204/415 |
| 3,429,796 | 2/1969 | Lauer | 204/195 |
| 3,510,420 | 5/1970 | Mills | 204/195 |
| 3,577,332 | 5/1971 | Porter et al. | 204/408 |
| 3,708,412 | 1/1973 | Lofgren | 204/195 P |
| 3,767,552 | 10/1973 | Lauer | 204/195 P |
| 4,017,373 | 4/1977 | Shaw et al. | 204/195 P |
| 4,126,531 | 11/1978 | Porter et al. | 204/408 |
| 4,132,616 | 1/1979 | Tantram et al. | 204/195 P |
| 4,477,403 | 10/1984 | Pust | 264/104 |
| 4,498,970 | 2/1985 | Chand | 204/415 |
| 4,686,011 | 8/1987 | Jäckle | 204/1 T |

FOREIGN PATENT DOCUMENTS 1442303 7/1976 United Kingdom ................ 204/403

OTHER PUBLICATIONS

R. V. Stuart, "Vacuum Technology, Thin Films, and Sputtering", 138-140 (1983).

Primary Examiner—G. L. Kaplan
Attorney, Agent, or Firm—Fulwider, Patton, Lee & Utecht

[57] ABSTRACT

An electrochemical gas sensor having a flexible membrane mounted at the sensing end of a housing, to dissipate increased electrolyte pressure, a small sensing electrode cooperating with a relatively thick porous sheet of polytetrafluoroethylene (PTFE) supported by the flexible membrane, and the housing also containing an electrolyte and a counter electrode, with suitable circuitry connected to the electrodes for quantifying the current generated by the sensor.

11 Claims, 2 Drawing Sheets

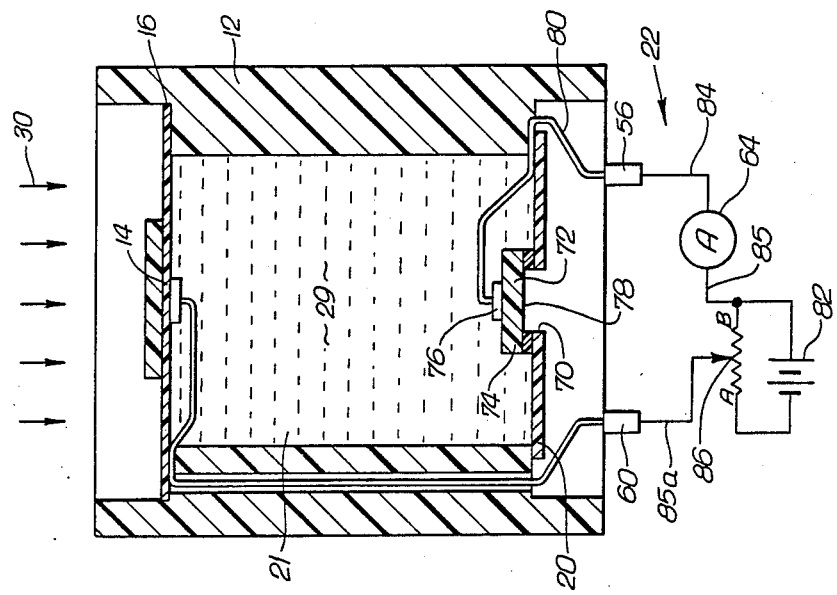
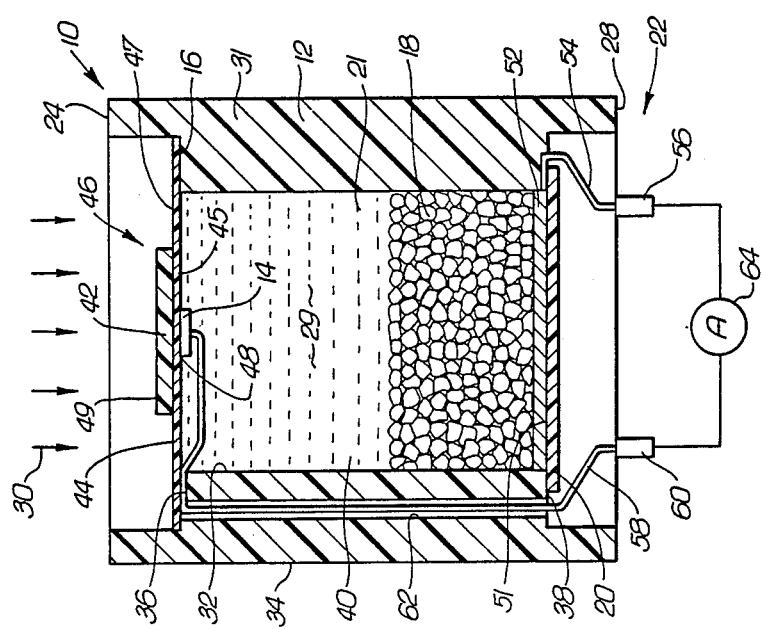

GAS SENSOR

This application is a continuation of Ser. No. 891,233 filed July 29, 1986 and now abandoned.

BACKGROUND OF THE INVENTION

This invention relates generally to electrochemical gas sensors and, more particularly, to an improved sensing electrode structure for electrochemical gas sensors. Gas sensors of this type are used to measure the partial pressure of a gas in a mixture of gases. For example, by appropriate selection of components, a gas sensor can indicate the concentration of oxygen in air. Other sensors indicate the concentrations of carbon monoxide, sulfur dioxide, oxides of nitrogen, hydrogen sulfide, and various other gases.

Basically, an electrochemical gas sensor of the type with which the invention is concerned includes a container in which there are disposed an electrolyte, a sensing electrode, and a counter electrode. When a gas to be sensed is introduced into the electrolyte adjacent to the sensing electrode, ions are formed and act as current carriers. A measurable current can then be detected in an external circuit connected to the electrodes.

There are two basic categories of sensors of this general type. One is the galvanic type, in which the counter electrode and electrolyte are selected to provide a measurable current without any external voltage source being necessary. For example, the use of lead or cadmium as a counter electrode, in an alkaline electrolyte, provides a galvanic sensor for the measurement of oxygen concentration. Also, the use of lead dioxide or manganese dioxide as the counter electrode, in an acid electrolyte, provides a galvanic sensor for the measurement of concentrations of carbon monoxide, hydrogen sulfide, and sulfur dioxide. A polarographic sensor is a second detector type, in which the counter electrode is made of material requiring the use of an external voltage source to make the sensor operate. The magnitude of the required external voltage will depend on such factors as the nature of the counter electrode, the acidity (pH) of the electrolyte, and the gas to be measured. The present invention is not limited to either the galvanic or the polarographic type of sensor.

An important consideration in one application of gas sensors is that the readings obtained should be proportional to the partial pressure of the gas to be measured. For example, in monitoring the partial pressure of oxygen in air for health reasons, the reading should reflect changes in total air pressure, even though the oxygen concentrations may not have changed In other words, the sensor should be indicative of the total amount of oxygen available, which is proportional to partial pressure, rather than indicative of the concentration of oxygen by weight or volume.

Responsive to these problems, the inventor received U.S. Pat. No. 4,498,970 issued Feb. 12, 1985, for an Electrochemical Gas Sensor the disclosure of which is incorporated by reference herein.

It has since been discovered that abrupt temperature changes in the sensor's operating environment can affect its detecting abilities. This rapid temperature change induced a thermal expansion of the electrolyte, which raised the pressure of the solution This increased pressure affected the gas solubility characteristics of the electrolyte, distorting the sensor readings. In addition, the increased electrolyte pressure separated the sensing electrode from the porous sheet. As a result, the sensor performance decreased, and gas diffusion time increased. Consequently, users of the sensor were required to thermally re-equilibrate the sensor or, alternatively, raise the test sample and sensor temperature in a step-wise fashion to the desired level. This precluded a rapid and spontaneous testing of the sample.

One proposed solution to this problem is set forth in U.S. Pat. No. 3,767,552 issued Oct. 23, 1973, to J. M. Lauer and provides a galvanic dual membrane system to allow for expansion of the electrolyte solution. In the Lauer sensor, increased pressure within the electrolyte chamber is dissipated by the expansion of a flexible membrane into a juxtaposed expansion chamber. Since this expansion chamber is also open to air distinct from the test sample, gases in the expansion chamber may diffuse into the electrolyte chamber through the flexible membrane and distort the sensor readings.

It will be appreciated from the foregoing that there is still a significant need in the gas sensing field for an electrochemical sensor that overcomes the aforementioned problems of the prior art. In particular, what is needed is a sensor with a relatively low working current, to provide a long useful life, insensitivity to temperature variations, and the ability to respond relatively quickly to changes in partial pressure of the sensed gas. The present invention clearly satisfies all of these requirements.

SUMMARY OF THE INVENTION

In accordance with the present invention an improved sensing electrode structure is provided that results in a low sensitivity to temperature variations and a rapid response to changes in the partial pressure of the sensed gas.

Briefly, and in general terms, the present invention comprises a sensor body having a sensing end and a hollow interior. An electrolyte is disposed within said sensor body. A flexible membrane adjacent the sensing end of the sensor body provides a means allowing for the expansion of the electrolyte solution. A sensing electrode or cathode is mounted upon the flexible membrane to move relative to the sensor body. A rigid support member is mounted adjacent the back end of the sensor body. A counter electrode or anode is mounted upon the rigid support member. The electrolyte electrically communicates both electrodes by contacting them. An electrical circuit connected to the electrodes, quantifies the current generated as a result of the diffusion of gas contacting said sensor, and thus measures the partial pressure of the gas being tested.

Additional embodiments of the invention include polarographic circuitry when the use of non-polarizable electrodes are used. A three-electrode system may also be provided to reduce the variation of the current generated by the exposure of the present invention to the gas sample.

It will be appreciated from the foregoing that the present invention represents a significant advance in the field of electrochemical gas sensing. In particular, the incorporation of a flexible member near the sensing end, to support the electrode and allow for electrolyte expansion, results in a rapid adaptation to sudden fluctuations in operating temperatures. The above and other aspects and advantages of the invention will become apparent from the following more detailed description, taken in conjunction with the accompanying drawings.

BRIEF DESCRIPTION OF THE DRAWINGS

FIG. 1 is a longitudinal, sectional view of a galvanic electrochemical gas sensor constructed in accordance with the present invention;

FIG. 2 is a longitudinal, sectional view of a polarographic electrochemical gas sensor constructed in accordance with the present invention;

DETAILED DESCRIPTION

Figure 4:
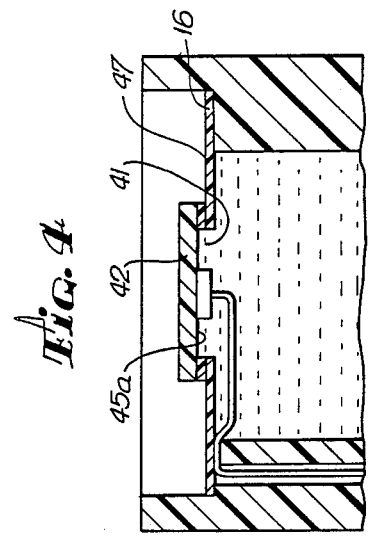
FIG. 4, is a fragmentary, sectional view, similar to FIG. 1, but illustrating an alternative construction of the present invention.

As shown in the exemplary drawings for the purposes of illustration, the present invention is principally concerned with improvements in electrochemical gas sensors. A gas sensor assembly, referred to generally by the reference numeral 10 in FIG. 1, is provided with a novel construction, which results in increased volumetric flexibility.

Figure 3:
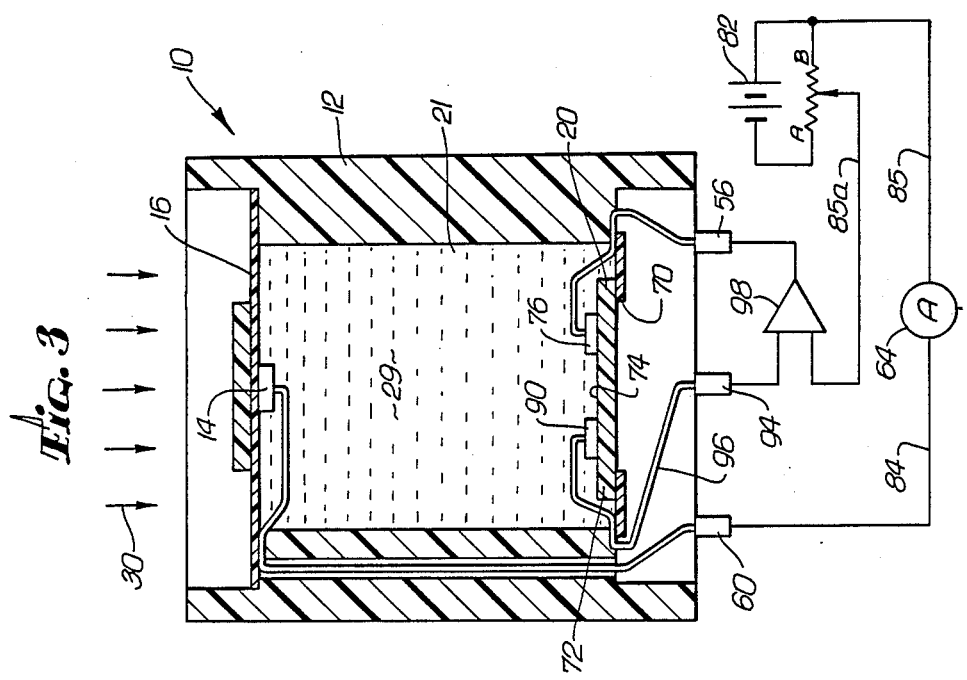
FIG. 3 is a longitudinal, sectional view of a three-electrode electrochemical gas sensor constructed in accordance with the invention.

As shown in FIGS. 1-3, the gas sensor 10 includes a support element or sensor body 12 having a sensing electrode or cathode 14 mounted on a flexible membrane 16. The flexible membrane 16 is mounted adjacent the sensor end exposed to the test sample. A counter electrode or anode 18 is mounted upon a rigid support member or plate 20, forming a bottom closure for the sensor body 12 adjacent the end opposite from the flexible membrane 16. A suitable electrolyte 21 is contained within the sensor body 12. An electrical circuit, generally designated 22, quantifies the current generated, the current being proportional to the partial pressure of the gas reaching the first electrode 14.

The improved electrochemical gas sensor of the present invention provides a relatively inexpensive and simple apparatus for enabling a sensor to adapt to sudden fluctuations in operating temperatures and pressures The flexible membrane enables the sensor to expand in response to increased electrolyte pressure, mitigating its effects. The annular flexing construction incorporates a protective sandwich electrode structure which increases sensor ruggedness. Furthermore, placing the flexible member on the sensing side and providing a rigid back member, reduces the sensor's exposure to gas sources other than the test sample, providing a less distorted and more reliable reading. Thus, not only does this construction ease assembly, but it reduces distortion and erratic readings.

More specifically, a sensor body 12 provides means for supporting and positioning the other various elements of the sensor structure. As shown in FIGS. 1-4, the sensor body 12 has a "sensing" end 24, a back end 28, and a hollow interior or cell chamber 29. The sensing end 24 is defined as the end which is exposed or closer to the test sample, indicated by the arrows 30. In one preferred form, the sensor body 12 is a tubular member including a wall 31 having an inside surface 32, an outside surface 34, and a typical outside diameter of 1.25 inches. A first annular shoulder 36, extending radially inward from the wall 31, is recessed longitudinally inward, adjacent the sensing end 24. A second annular shoulder 38, extending radially inward from the wall 31, is recessed longitudinally inward adjacent the back end 28. An axial passageway 40, defined by the sensor body 12, passes substantially unrestricted from the sensing end 24 to the back end 28. In one preferred form, the axial passageway 40 is an axial longitudinal bore of about 0.825 inches in diameter. The sensor body is, in one preferred form, of an electrolyte resistant material such as polyvinylchloride (PVC).

Closing the sensing end 24 of the sensor body 12 is a solid electrolyte impermeable, flexible membrane 16. By this construction, the flexible membrane 16 is interposed between the test sample and the cell chamber 29. The flexible membrane 16 is mounted circumferentially upon first shoulder 36 of the sensor body 12, preferably by adhesive or conventional heat-sealing techniques. In one form, the membrane 16 may be formed of a polytetrafluoroethylene (PTFE) or polyethylene material, although any electrolyte resistant and flexible material may be sufficient. An example of PTFE material may include synthetic resin polymers sold under the trademark Teflon (the trademark is owned by E.I. DuPont Nemours & Co. of Wilmington, Del.). In this form, the membrane 16 is in the range of one-eight to two mils thick (one mil equalling one-one thousandth of an inch or 0.0254 millimeters). In another form, as shown in FIG. 4, the flexible membrane may be an annular member having a centrally disposed aperture 41. The aperture 41 may be in the range of one-eighth to one-half inch in diameter. In this form, the membrane 16 may be a sheet of non-gas permeable material, for example plastic film formed of polyethylene terephthalate sold under the trademarks Mylar (the trademark is owned by E.I. DuPont Nemours & Co. of Wilmington, Del.), synthetic resin polymers sold under the trademark Teflon, or polyethylene, in the range of two to fifteen mils thick.

As shown in FIGS. 1 and 4, a relatively thick sheet 42 of porous PTFE material is mounted substantially co-axially upon the flexible membrane 16. The sheet 42 is preferably about fifty to sixty mils thick, with a pore size of two to ten microns The outer surface 43 of the sheet 42 is exposed to a gas sample being analyzed, as indicate by the arrows 30. As shown in FIG. 1, the porous sheet 42 may be mounted upon the outer surface 44 of the membrane 16. In another form, as shown in FIG. 4, the porous sheet 42 may be circumferentially mounted adjacent the aperture 41 in sheet 16.

A sensing electrode or cathode 14 is disposed adjacent the sensing end 24 of the housing 12. As shown in FIG. 1, in one form, the sensing electrode 14 is disposed on the inner surface 45 of the flexible membrane 16. As shown in FIG. 4, the sensing electrode 14 may be disposed on the inner surface 45a of the porous sheet 42. The sensing electrode 14 is positioned and cooperates with the sheet 42 and flexible membrane 16 to form a rigid sandwich structure generally designated by the numeral 46. As an annular portion 47 of the flexible membrane 16 bows in response to electrolytic pressure changes, the attached sensing electrode moves with it.

In one preferred form, the sensing electrode 14 is a small area 48 of powdered metal impregnated by the application of pressure to the surface upon which it is disposed. The procedure is more specifically described in the inventor's U.S. Pat. No. 4,498,970, issued Feb. 12, 1985. The invention also may include the deposition of the noble metal powder (i.e., platinum, gold or silver) upon either the membrane 16, as shown in FIG. 1 or upon the porous sheet 42 as shown in FIG. 4. Another embodiment may include the incorporation of conventional metal sheets or mesh into the sensing electrode 14's construction, as described in U.S. Pat. No.

3,429,796, issued Feb. 15, 1969 to J. M. Lauer. In whatever form selected, the sensing electrode 14 cooperates with the porous sheet 42 to form a rigid sandwich 46 which moves relative the sensor body 12 with the flexible membrane 16.

As shown in FIG. 1, a rigid support member or plate 20 forms the bottom closure for the sensor body 12 on the back end 28 opposite the sensing end 24. In one preferred form, said rigid member 20 is formed of a polyvinylchloride (PVC) material mounted upon the inside surface 51 of the rigid member 20 is a washer or contact plate 52, formed of an electrically conducting metal, for example stainless steel, which is resistant to the electrolyte 21 contacted therewith The contact plate 52 provides an external electrical contact through a connecting wire 54 to the first terminal 56. The rigid support member 20 rests upon the second annular shoulder 30, recessed within the sensor body 12. This support member 20 is mounted by adhesive or by conventional heat-sealing methods.

Furthermore, as shown in FIG. 1, a counter electrode or anode 18 may be formed from a plurality of lead particles 40-100 mesh in size. While lead particles are preferable, other nonpolarizable metals can be used, including but not limited to cadmium, antimony, and zinc. These particles are generally distributed uniformly over the entire surface of the contact plate 52. Typically ten grams of said lead particles enables the sensor 10 to operate about twelve months.

A suitable electrolyte 21, for example an aqueous solution of potassium hydroxide, fills the interior 31 defined by the flexible membrane 16, the sensor body 12 and the rigid plate 20. This solution completely covers over the counter electrode 18, fills the space between the electrode 18 and the sensing electrode 14 and contacts the lowermost side of the sensing electrode 14. While an oxygen gas sensor could use potassium hydroxide as an electrolyte, the selection of the particular electrolyte and its chemical parameters (such as pH) depends largely in part upon the particular gas to be analyzed. For example, for some toxic gases, an acid electrolyte is appropriate. However, such choices are well-known in the art and will not be addressed in detail herein.

A second connecting wire 58, preferably of platinum, is bonded to the electrode 14 and connected at its other end to a second outside terminal 60. In one preferred form the wire 58 is of 0.010 inch diameter and 2.0 inch in length. The invention may include the use of platinum ribbons of similar dimensions to electrically communicate the electrode 14 with the terminal 60. A second axial passageway 62 defined by the sensor body 12, provides a means for communicating the wire 58 through the sensor body 12. Alternatively, apertures (not shown) may be formed in the sensor body 12, to allow the wire to pass through the sensor body wall 31 and run longitudinally along the sensor body's external surface 34.

As shown in FIGS. 1-4, electrical circuit 22 includes an ammeter or galvanometer 64 connected across the terminals 56 and 60, to provide means for measuring or quantifying the depolarizing current generated by the sensor and thus a measure of the partial pressure of the gas reaching the sensing electrode 14. It is generally well-known in the art that operational amplifiers are included within the ammeter 64 to increase its sensitivity to small currents.

In addition, as shown in FIGS. 2 and 3, the invention may include polarographic embodiments which use the aforementioned expandable construction in conjunction with polarizable electrodes. These structures are useful in detecting toxic gases such as $H_2S$, $CO$, $SO_2$, $NO_2$, $Cl_2$, etc. The construction of the sensor body 12, and sensing electrode 14, and flexible membrane 16 are the same as earlier described and need not be discussed in detail herein. In one preferred form, the rigid plate 20 is an annular member having an aperture 70 formed therein. The aperture 70 is in the range of about one-eighth to one-half inch in diameter In this form, the plate 20 may be a sheet of electrolyte resistant material, such as polyethylene or PVC, 100-200 mils thick.

In this preferred form, the counter electrode 18, rather than being particles of lead or other non-polarizable materials, comprises a polarizable electrode 76, similar in structure to the first sensing electrode 14. This polarizable electrode 76, positioned upon the inside surface 74 of a second porous PTFE sheet 72, cooperates with the second sheet 72 to form a rigid sandwich. The outer surface 78 of second sheet 72 contacts ambient air.

While in the galvanic form, as shown in FIG. 1, the support member 20 prevents exposure of the sensor interior to air, in the alternative polarographic forms, as shown in FIGS. 2 and 3, exposure of the polarizable electrode 76 and reference electrode 90 to air is provided as a reference voltage or EMF. The aperture 70 provides this means for communicating air to the electrodes 76 and 90. Wire 80 connected at opposite ends to the polarizable electrode 76 and first terminal 56 provides means for electrically communicating those respective structures.

As shown FIG. 2, circuit 22 may include a conventional potentiometric circuit consistent with Poggendorff's compensation method, to provide means for comparing and quantifying the current generated by exposing the sensor 10 to the test sample. Reference battery 82 provides means for providing an external potential of a known electromotive force (EMF) impressed across a uniform resistance AB. Preferably, standard lithium or nickel-cadmium batteries may be used, the only requirement being that the potential source be of a required, known EMF. First terminal 56 is connected through the ammeter or galvanometer 64 to point B by wires 84 and 85, providing means to electrically communicate the terminal, reference battery and point B. The second terminal 60 is connected by wire 85a with the sliding or step contact 86 and uniform resistance AB. While the circuit 22 as specifically described provides a comparison and determination of current generated by polarizable electrodes, it will be understood that the example so given is not intended to limit the scope of the invention, but offered solely for the purposes of illustration. For example, the potentiometric circuit may also be used with non-polarizable electrodes, e.g., lead, lead dioxide, and silver. Furthermore, the selection of the voltage and the type of material used as the polarizable electrode 76 depends upon the gas to be analyzed. However, as with the electrolyte selection, such requirements are well documented in the art and need not be addressed herein.

As shown in FIG. 3, a three electrode system is used to provide a means for regulating the applied external potential. The three electrode system regulates the bias voltage to a fixed level to avoid variations in the output. A third or reference electrode 90 is disposed adjacent to the polarizable electrode 76 on the inside surface 74 of the second porous but rigid sheet 72. The third electrode 90 is in electrical communication with a third external terminal 94 by wire 96. First and third terminals 56 and 94 are in communication with a potentiostat amplifier 98 which reduces the signal variation difference before inserting it into the conventional potentiometric circuit as earlier described.

In operation, the sensor 10 is connected into a probe holder (not shown) and exposed to the medium carrying the test sample. In one form, as shown in FIG. 1, the thick sheet 42 and flexible membrane 16 permit the permeation of the gas examined into the cell chamber 29 at a rate proportional to the concentration of the gas being examined In another form, as shown in FIG. 4, the thickness of the flexible membrane 16 may limit the gas permeation to through the aperture 41. In one preferred form, as shown in FIG. 1, since the flexible, gas permeable membrane 16 is only exposed to the gas examined and the cell chamber, the test gas is not affected by atmospheric gas levels in the air. In the other preferred forms, as shown in FIGS. 2 and 3, the potentiometric circuitry compensates for this exposure and thus is not affected by atmospheric gas levels. On each side of the sheet 42 and membrane 16, since the concentration inside the cell is negligible when the cell is in dynamic equilibrium, the rate of influx of the gas is proportional to its concentration in the sample being tested. The gas reaching the sensing electrode 14 or cathode, is reduced to an anion which, in the case of oxygen, means that the anions are reduced to hydroxyl ions. Simultaneously, the anodically liberated lead ions form insoluble lead dioxide. A current corresponding to the rate of the above reactions flows in the external circuit 22 as indicated on the ammeter 64.

In situations of rapid temperature fluctuations, the flexible annular member allows for the rigid sandwich to move along the sensor's longitudinal axis. As a result, an increased volume is provided for the thermal expansion, dissipating the resultant effects As such, the gas solubility affects of minute gas concentrations are mitigated, enabling quick responses to low gas concentrations. Furthermore, by placing the flexible member adjacent the sensing end and exposing the cell chamber 29 only to the test sample, distortion is also minimized. For example in determining oxygen concentration, wide variations in the operating temperatures on the order of 25 degrees Fahrenheit do not affect quick responses in the ranges of zero to one thousand parts per million.

It will be appreciated from the foregoing that the present invention represents a significant advance in the field of electrochemical gas sensing. In particular, the present invention provides a flexible membrane between the test sample and the electrolyte chamber, dissipating electrolyte pressure without introducing gases outside the test sample into the sensor. This results in low sensor sensitivity to temperature changes and a rapid sensor response to changes in the partial pressure of the gas being measured. It will also be appreciated that, although presently preferred embodiments of the invention have been described by way of example, various modifications may be made without departing from the spirit and scope of the invention. Accordingly, the present invention is not to be limited except as by the appended claims.

what is claimed is:

1. An electrochemical gas sensor which is relatively insensitive to variations in ambient conditions, comprising:
    (a) a hollow sensor body which contains electrolyte and has an open sensing end;
    (b) a flexible closure which extends across the open sensing end of the sensor body and which has at least an outer annular section formed of an electrolyte impermeable flexible membrane;
    (c) a sensing electrode in contact with the electrolyte which has an outer surface and smaller diametrical dimensions than the flexible closure;
    (d) an electrolyte impermeable, gas permeable material covering the outer surface of the sensing electrode; and
    (e) a support member secured to the sensing electrode forming therewith a relatively rigid sandwich structure centrally located on said closure and secured to the annular section thereof.

2. The electrochemical gas sensor of claim 1 wherein the electrolyte impermeable, gas permeable material is over the sensing electrode is in the form of porous sheet.

3. The electrochemical gas sensor of claim 2 wherein the porous sheet is made from a material selected from the group consisting of polyethylene and polytetrafluoroethylene.

4. The electrochemical gas sensor of claim 2 wherein the porous sheet is about 50 to about 60 mils thick.

5. The electrochemical gas sensor of claim 2 wherein the porous sheet has a pore size of about 2 to about 20 microns.

6. The electrochemical gas sensor of claim 1 wherein the flexible membrane of the closure member is formed of a material selected from the group consisting of polytetrafluoroethylene, polyethylene, and polyethylene terephthalate.

7. The electrochemical gas sensor of claim 1 wherein the flexible membrane is about 2 to about 15 mils thick.

8. The electrochemical gas sensor of claim 1 including a counter electrode which is in electrical contact with the electrolyte and which is spatially disposed from the sensing electrode.

9. The electrochemical gas sensor of claim 8 including a potentiometric circuit electrically connected to the sensing and counter electrodes.

10. The electrochemical gas sensor of claim 9 wherein the potentiometric circuit includes a means to provide an external electrical potential and means for regulating the external potential.

11. The electrochemical gas sensor of claim 1 wherein the closure comprises an electrolyte impermeable, gas permeable plastic film and the sensing electrode is mounted on the inside surface thereof.

* * * * *